(12) United States Patent
Hung et al.

(10) Patent No.: US 6,585,706 B2
(45) Date of Patent: Jul. 1, 2003

(54) APPARATUS, METHODS AND KITS FOR SIMULTANEOUS DELIVERY OF A SUBSTANCE TO MULTIPLE BREAST MILK DUCTS

(75) Inventors: David Hung, Belmont, CA (US); Xuanmin He, Palo Alto, CA (US)

(73) Assignee: Cytyc Health Corporation, Boxborough, MA (US)

( * ) Notice: Subject to any disclaimer, the term of this patent is extended or adjusted under 35 U.S.C. 154(b) by 0 days.

(21) Appl. No.: 10/072,911

(22) Filed: Feb. 12, 2002

(65) Prior Publication Data

US 2002/0107502 A1 Aug. 8, 2002

Related U.S. Application Data (62) Division of application No. 09/506,477, filed on Feb. 29, 2000, now Pat. No. 6,398,765.
(60) Provisional application No. 60/122,076, filed on Mar. 1, 1999, provisional application No. 60/134,613, filed on May 18, 1999, provisional application No. 60/143,476, filed on Jul. 12, 1999, provisional application No. 60/143,359, filed on Jul. 12, 1999, and provisional application No. 60/170,997, filed on Dec. 14, 1999.

(51) Int. Cl.⁷ .......................... A61M 25/00; A61M 1/06
(52) U.S. Cl. ........................... 604/284; 604/74
(58) Field of Search ................ 604/284, 29, 73, 604/74, 514, 94.01

(56) References Cited

U.S. PATENT DOCUMENTS

| | | |
|---|---|---|
| 3,608,540 A | 9/1971 | Sartorius |
| 3,786,801 A | 1/1974 | Sartorius |
| 3,821,956 A | 7/1974 | Gordhammer et al. |
| 4,406,653 A | 9/1983 | Nunez |
| 4,543,087 A | 9/1985 | Sommercorn et al. |
| 4,613,329 A | 9/1986 | Bodicky |
| 4,739,768 A | 4/1988 | Engelson |
| 4,790,830 A | 12/1988 | Hamacher |
| 4,795,424 A | 1/1989 | Barner et al. |
| 4,878,903 A | 11/1989 | Mueller |
| 4,925,452 A | 5/1990 | Melinyshyn et al. |
| 4,957,484 A | 9/1990 | Murtfeldt |
| 5,176,647 A | 1/1993 | Knoepfler |
| 5,183,470 A | 2/1993 | Wettermann |
| 5,279,551 A | 1/1994 | James |
| 5,300,022 A | 4/1994 | Klapper et al. |
| 5,322,519 A | 6/1994 | Ash |
| 5,333,609 A | 8/1994 | Bedingham et al. |
| 5,350,358 A | 9/1994 | Martin |
| 5,364,344 A | 11/1994 | Beattie et al. |
| 5,368,574 A | 11/1994 | Antonacci et al. |
| 5,593,393 A | 1/1997 | Trudell et al. |

(List continued on next page.)

FOREIGN PATENT DOCUMENTS

EP 448395 9/1991

OTHER PUBLICATIONS

Papanicolaou et al, Exfoliative Cytology Of The Human Mammary Gland And Its Value In The Diagnosis Of Cancer And Other Diseases Of The Breast, Cancer, vol. 11, pp 377–409, 1958.

Goodson WH & King EB, Chapter 4: Discharges and Secretions of the Nipple, The Breast: Comprehensive Management of Benign and Malignant Diseases, 2$^{nd}$ Ed., Bland & Kirby Eds. W.B. Saunders Col, Philadelphia PA, vol. 2, pp 51–74, 1998.

(List continued on next page.)

Primary Examiner—Sharon Kennedy
(74) Attorney, Agent, or Firm—Banner & Witcoff, Ltd.

(57) ABSTRACT

Apparatus, methods and kits for simultaneous delivery of a fluid or other substance to two or more breast milk ducts are provided. The fluid can be delivered for a variety of purposes including lavage of the ducts and administering an agent for therapeutic, prophylactic, or diagnostic purposes.

16 Claims, 4 Drawing Sheets

U.S. PATENT DOCUMENTS

| | | | |
|---|---|---|---|
| 5,599,324 | A | 2/1997 | McAlister |
| 5,637,102 | A | 6/1997 | Tolkoff et al. |
| 5,649,909 | A | 7/1997 | Cornelius |
| 5,683,420 | A | 11/1997 | Jeter et al. |
| 5,683,640 | A | 11/1997 | Miller et al. |
| 5,702,365 | A | 12/1997 | King |
| 5,704,925 | A | 1/1998 | Otten et al. |
| 5,795,326 | A | 8/1998 | Siman |
| 5,797,869 | A | 8/1998 | Martin et al. |
| 5,807,329 | A | 9/1998 | Gelman |
| 5,810,789 | A | 9/1998 | Powers et al. |
| 5,810,867 | A | 9/1998 | Zarbatany et al. |
| 5,827,237 | A | 10/1998 | Macoviak et al. |
| 5,891,111 | A | 4/1999 | Ismael |
| 5,904,715 | A | 5/1999 | Jeter et al. |
| 6,221,622 | B1 * | 4/2001 | Love .......................... 435/7.23 |

OTHER PUBLICATIONS

King et al, Nipple Aspirate Cytology for the Study of Breast Cancer Precursors, Journal of the National Cancer Institute, vol. 71(6), pp 1115–1121, 1983.

Wrensch et al, Breast Cancer Incidence in Women with Abnormal Cytology in Nipple Aspirates of Breast Fluid, Am. J. Epidemiology, vol. 135 (2), pp 130–141, 1992.

Sauter et al, Nipple aspirate fluid: a promising non–invasive method to identify cellular markers of breast cancer risk, British Journal of Cancer, vol. 76 (4), pp 494–501, 1997.

Sartorius et al, Cytologic Evaluation of Breast Fluid in the Detection of Breast Disease, Journal of the National Cancer Institute, vol. 59 (4), pp 1073–1080, 1977.

Love and Barsky, Breast–duct endoscopy to study stages of cancerous breast disease, Lancet, vol. 348(9033), pp 997–999, 1996.

Makita et al, Duct endoscopy and endoscopic biopsy in the evaluation of the nipple discharge, Breast Cancer Res Treat vol. 18, pp 179–188, 1991.

Okazaki et al, Fiberoptic Ductoscopy of the Breast: A New Diagnostic Procedure for Nipple Discharge,, Jpn J. Clin. Oncol. vol. 21, pp 188–193, 1991.

Petrakis, Studies on the Epidemiology and Natural History of Benign Breast Disease and Breast Cancer Using Nipple Aspirate Fluid, Cancer Epidemiology, Biomarker Prev., vol. 2, pp 3–10, 1993.

Petrakis, Psysiologic, biochemical, and cytologic aspects of nipple aspirate fluid, Breast Cancer Res. Treat, vol. 8, pp 7–19, 1986.

Wrensch et al, Breast Cancer Res Treat, Factors associated with obtaining nipple aspirate fluid: Analysis of 1428 women and literature review, vol. 15, pp 39–21, 1990.

Wrensch et al, Breast Fluid Cholesterol and Cholesterol B–Epoxide Concentrations in Women with Benign Breast Disease, Cancer Res., vol. 49,pp 2168–2174, 1989.

Mechincal Engineering, vol. 118 (10), pp 65–68, 1996.

King et al, Analytic Studies of Foam Cells From Breast Cancer Precursors, Cytometry, vol. 5, pp 124–130, 1984.

King et al, Cellular Composition of the Nipple Aspirate Specimen of Breast Fluid, A.J.C.P., vol. 64, pp 739–748, 1975.

Masood et al, The Missin Link: A "Pap Smear" For Early Breast Cancer Detection and Prevention, The Breast Journal, vol. 5, pp 1–2, 1999.

Sartorius et al, Cytologic Evaluation of Breast Fluid in the Detection of Breast Disease, Journal of National Cancer, vol. 59, pp 1073–1080, 1977.

Sauter et al, Nipple aspirate fluid: a promising non–invasive method to identify cellular markers of breast cancer risk, British J. Cancer, vol. 76(4), pp 494–501, 1997.

Wrensch et al, Breast Cancer Incidence in Women with Abnormal Cytology in Nipple Aspirates of Breast Fluid, Amer J. Epid., vol. 135, pp 130–141, 1992.

Frykberg and Masood Copeland EM 3d Bland KI., (Ductal Carcinoma in situ of the breast) Surgery, Gynecology & Obstetrics, vol. 177 (4), pp. 425–440, 1993.

Barsky, et al. "Pathologic analysis of breast duct endoscoped mastectomies" Proc Annual Meeting Am Assoc. Cancer res 34,abstract #67.

"Breast Fluid cells help in early cancer detection" JAMA May 7, 1973 vol. 224, No. 6.

Leborgne "The Breast in roentegen diagnosis." Uruguay 1953.

Love & Barsky. "Breast–duct endoscopy to study stages of cancerous breast disease." The Lancet vol 348 Oct. 12, 1996 pp 997–999.

Makita, et al. "Duct endoscopy and endoscopic biopsy in the evaluation of nipple discharge." Breast Cancer Research and Treatment 18: 179–188 1991.

Okazaki, et al. "Relationship between cytologic results and the extent of intraductal spread in nonpalpable breast cancers with nipple discharge" Tumor Res. 31, 89–97 (1996).

Okazaki et al, "Fiber optic ductoscopy of the breast" Jpn J Clin Oncol 1991 21(3):188–193.

Papanicolaou, et al. "Exfoliative cytology of the human mammary gland and its value in the diagnosis of cancer and other diseases of the breast." Cancer Mar.–Apr. 1958, 11(2): 377–409.

* cited by examiner

APPARATUS, METHODS AND KITS FOR SIMULTANEOUS DELIVERY OF A SUBSTANCE TO MULTIPLE BREAST MILK DUCTS

CROSS-REFERENCES TO RELATED APPLICATIONS

This application is a divisional of U.S. Ser. No. 09/506,477 filed Feb. 29, 2000 now U.S. Pat. No. 6,398,765, issued Jun. 4, 2002. This application claims the benefit of each of the following provisional applications under 37 CFR §1.78: 60/122,076, filed Mar. 1, 1999; 60/134,613, filed on May 18, 1999; 60/143,476, filed on Jul. 12, 1999; 60/143,359, filed on Jul. 12, 1999; and 60/170,997, filed on Dec. 14, 1999. The application is also related to non-provisional application Ser. No. 09/473,519, filed on Dec. 28, 1999. The full disclosures of each application are incorporated herein by reference.

BACKGROUND OF THE INVENTION

1. Field of the Invention

The present invention relates generally to medical devices and methods. More particularly, it relates to devices and methods for the delivery of substances to breast milk ducts.

2. Background of the Invention

The current state of the ductal access art is that the ducts in a breast are accessed one-by-one with a catheter. The human breast has from 6–12 ducts. This process of duct-by-duct access has many disadvantages, including that the process is slow and that it is very difficult after finishing lavage of one duct to know which of the other ducts of a breast have or have not been lavaged. Thus, under the one-duct-at-a-time duct lavaging or accessing system it is easy to miss a duct or access or duct twice. The present invention at least partly overcomes these deficiencies.

U.S. Pat. No. 5,763,415 to Sukumar claims a method of treating the ductal epithelium of a mammary glad prophylactically for cancer by ductal cannulation and administration of a vector comprising thymidine kinase into the duct. The delivery of epithelium-destroying agents to breasts by ductal cannulation is described in WO 97/05898.

Various methods and techniques of duct-by-duct access have been described, including methods described in Love and Barsky, (1966) Lancet 348: 997–999, and Presentations about ductal access made in Love, (1992) "Breast duct endoscopy: a pilot study of potential technique for evaluating intraductal disease," presented at 15th Annual San Antonio Breast Cancer Symposium, San Antonio, Tex., Abstract 197; Barsky and Love (1996) "Pathological analysis of breast duct endoscoped mastectomies," Laboratory Investigation, Modern Pathology, Abstract 67; and Lewis (1997) Biophotonics International, pages 27–28, May/June 1997.

A company called Diagnostics, Inc. formed in 1968, produced devices to obtain breast ductal fluid for cytological evaluation. The devices included a breast duct catheter to infuse fluid into and collect fluid from individual ducts. The devices were sold prior to May 28, 1976 for the purpose of collecting breast ductal fluid for cytological evaluation.

A patent application entitled "Methods and kits for obtaining fluid and cellular material from breast ducts, " U.S. Ser. No. 09/067,661 filed Apr. 28, 1998, and its continuation-in-part, U.S. Ser. No. 09/301,058 filed Apr. 28, 1999, describe and claim infusing a small amount of fluid into the duct and collecting the fluid using a catheter. Related applications include U.S. Ser. No. 60/143,476 and 60/143,359, both filed Jul. 12, 1999, 60/134,613, filed May 18, 1999, and 60/114,048 filed Dec. 28, 1998, all of which are herein incorporated by reference in their entirety. Provisional application No. 60/170,997, filed Dec. 14, 1999, and non-provisional application Ser. No. 09/473,510, filed Dec. 28, 1999 describe methods and apparatus for delivering a substance to a breast duct.

SUMMARY OF THE INVENTION

Apparatus for accessing two or more ductal networks in a breast comprise two or more individual access probes, each probe having a lumen and being configured for insertion through an orifice of a ductal network. The apparatus further comprises a manifold having an inlet for receiving a fluid and two or more outlets, one each for distributing and/or collecting the fluid to each of the probe lumens. The manifold preferably connects to more than two probes, usually to at least three probes, more usually to at least six probes, and even more usually to at least twelve probes. Optionally, the probes may be selectively and removably connected to the manifold in any number up to the total number. In one embodiment, the total number of probes are pre-connected to the manifold and at least some of the probes have valves or other means for selectively closing the probe lumen. The apparatus can further comprise a pump that connects to the manifold to deliver and/or aspirate a fluid to the manifold. The pump can comprise a syringe that is pre-loaded with a wash or other fluid. Each probe lumen is optionally connectable to a collection lumen to collect a sample from each duct separately.

The apparatus can further comprise a plurality of fluid collection tubes, and the tubes are connected or connectable to the probe lumen. Thus is provided an apparatus for accessing a plurality of ductal networks in a breast, comprising a plurality of individual access probes, each probe having a lumen and being configured for insertion through an orifice of a ductal network; and a manifold having an inlet for receiving a fluid and a plurality of outlets for distributing the fluid to each of the probe lumens.

A method for delivering a substance to two or more ductal networks in a breast is provided comprising establishing access to two or more ductal network in the breast through a ductal orifice of each ductal network; and thereafter delivering a substance to and/or collecting a fluid from two or more of the ductal networks. Establishing access comprises inserting an access probe in each ductal orifice to be accessed. At least some of the access probes are fluidly connected by a manifold so that substance may be delivered simultaneously to the connected probes through the manifold. All of the access probes are fluidly connected to the manifold so that fluid may be delivered simultaneously to all probes. The substance is delivered simultaneously to all of the accessed ductal networks. Fluid can be collected in separate receptacles for each ductal network. The access can be established to each of the ductal networks in a breast.

A method for delivering a fluid to two or more ductal networks in a breast is provided comprising locating two or more ductal networks in a nipple of the breast; inserting an access probe through an orifice of each of the located ductal networks; and infusing the fluid through a manifold to each of the probes. The method further comprises connecting individual probes to the manifold so that the number of probes connected to the manifold is the same as the number of probes inserted into ductal orifices.

The method further comprises providing an assembly comprising a number of access probes greater than the number of ductal orifices. The access probes can be preloaded on the manifold, while selectively blocking those access probes connected to the manifold which are not inserted to a ductal network. The method can further comprise collecting fluid from each accessed ductal network, wherein the fluid is collected separately so that no one fluid from a ductal network is mixed with fluid from another ductal network.

A kit for delivering a substance to a two or more of ductal networks in a breast, is provided comprising two or more of probes each having a lumen and being configured for introduction into a ductal network of the breast, and instructions for use setting forth a method according to any of claims identified herein. A kit is also provided comprising a manifold having an inlet and at least twelve outlets, and at least twelve access probes connectable to the outlets on the manifold. The access probes are configured for insertion through an orifice of a ductal network of a breast. The kit can further comprise a separate collection receptacle for each probe.

BRIEF DESCRIPTION OF THE DRAWINGS

FIGS. 2A, 2B, 2C1 and 2C2, are detailed cross-sectional views of the apparatus of FIG. 2.

DESCRIPTION OF THE SPECIFIC EMBODIMENTS

The following preferred embodiments and examples are offered by way of illustration and not by way of limitation.

Apparatus according to the present invention for accessing two or more ductal networks in a human breast comprises a manifold having two or more outflow ports connected or connectable to probes, catheters or other like members having lumens, each capable or accessing a breast duct and configured to infuse and optionally collect fluid or other infusible material into accessed breast ducts in a human breast. The manifold has an inlet for receiving fluid from a connectable fluid source, such as a pump or syringe, and a plurality (e.g. two or more) outlets for distributing the fluid to a lumen in each of the probes. Usually, the manifold will have a total of at least three, more usually at least six and preferably at least 12 outlets, thus providing capacity to connect 12 or more probes in order to access and infuse all of the average 9–12 ducts in a human breast. Optionally, the probes may be removably attached to the manifold outlets. Thus, depending on the number of ducts to be accessed in a procedure, the same number of probe lumens can be attached at outlets on the manifold. The inlet on the manifold receives fluid from a fluid source, e.g. a syringe, pump, or other fluid delivery unit capable of providing a fluid inflow under a controlled pressure to the manifold. The syringe, pump, or other fluid delivery unit can be pre-loaded with a fluid (in pre-measured volumes) or other material to be delivered to two or more ducts through the manifold. The fluid can comprise a substance and/or an agent to facilitate collecting ductal contents (e.g. to collect cells or other debris from the duct), or the fluid can comprise a substance and/or an agent that comprises e.g. a therapeutic agent, a prophylactic agent, or a diagnostic agent.

The outlets may additionally have valves or other elements to control fluid flow into the outlets and/or inhibit backflow of fluid from the duct, e.g. a stopcock or other such element. The fluid controlling elements can be at the manifold outlets or on the probe itself. Thus, at least some of the probes (e.g. two or more) can be pre-connected to the manifold and have means for selectively closing (or opening) the probe lumens, e.g. for receiving an infusion fluid from the manifold, or stopping any back flow from entering the manifold from the duct so that such material can be diverted to a separate collection receptacle, as described below. Such a control element is useful, e.g. where a duct has been filled and it is desired that any collectable fluid be isolated from other collectable fluids from the other ducts. The probe lumens might also be selectively closed after the ducts have been filled during a massaging of the breast, in order to retain fluid in the ducts and not allow it to flow back into the infusion lumens of the probes i.e. to keep it from leaving through the outlet in the manifold.

The probes will have an infusion lumen, e.g. which is directly connected to the manifold unit, and will preferably also have a collection lumen e.g. that branches from the infusion lumen for separately collecting fluid from each duct. Each probe will preferably have a separate collection tube having a lumen in order to collect a sample from each duct separately. Thus, the apparatus can comprise a plurality of fluid collection tubes, and the tubes will each be individually connected or connectable to individual probes. A fluid control valve can close the infusion lumen to inhibit backflow of collected fluid to the manifold, and/or to divert the collected fluid to the fluid collection receptacles. Thus the apparatus can be used for accessing a plurality of ductal networks in a breast with a plurality of individual access probes, each probe having a lumen and being configured for insertion through an orifice of a ductal network. A manifold having an inlet for receiving a fluid and a plurality of outlets distributes the fluid to each of the probe lumens, and optionally the fluid may then be collected through collection tubes which branch from the infusion lumens in the probes so that isolation of the collected fluids can be maintained.

Figure 1:
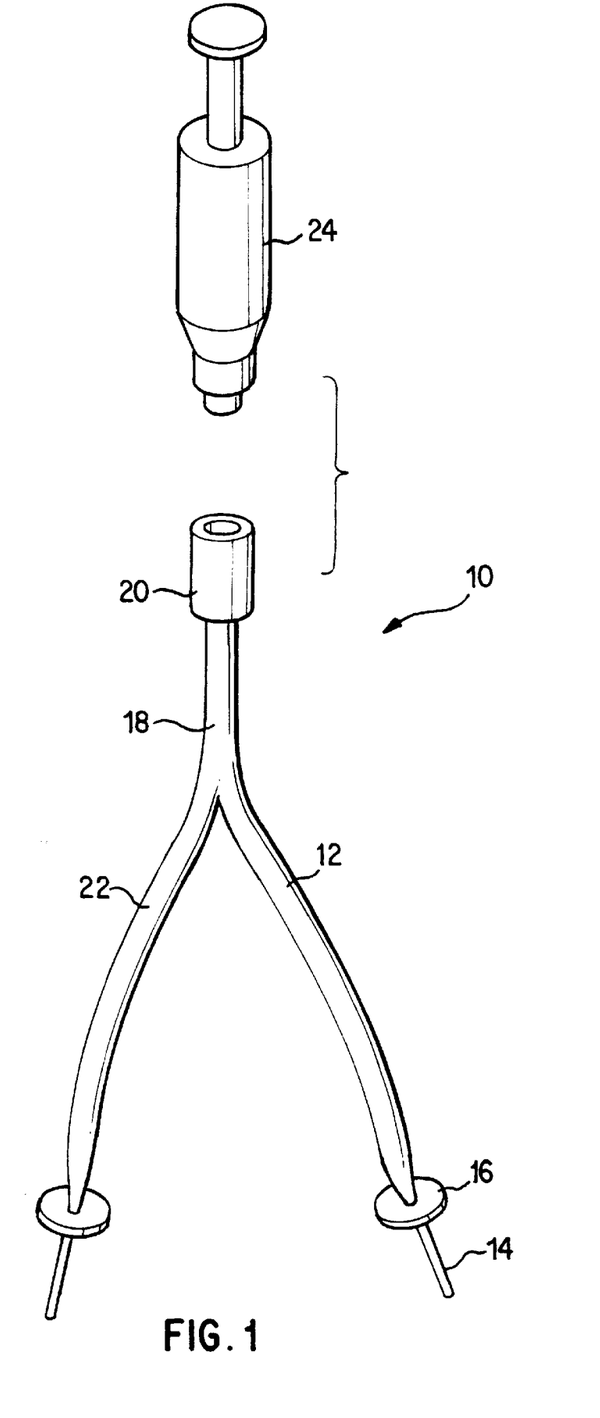
FIG. 1 shows a basic multiple duct infusion apparatus.

Turning now to the figures, FIG. 1 illustrates an apparatus 10 having a manifold structure 18 which branches into two probes 12 and 22. A manifold inlet 20 receives a fluid from a fluid source, such as syringe 24. Probe 12 has a stop 16 to prevent excessive penetration into the duct by tip 14. The stop can be a disk, flange, or other protrusion on the probe to prevent the probe from penetrating the duct passed a certain point. Useful dimensions for the probe and probe tip are described, for example, in copending application Ser. No. 09/473,510, the full disclosure of which has previously been incorporated by reference. Probes 12 and 22 have infusion lumens which are infused with fluid through manifold 18 and inlet 20 from fluid source 24. In addition, the probes that access the ductal networks can have some form of attachment member to attach the probe or lumen to the duct to keep it from falling out of the duct once the duct is accessed. This could be an enlarged segment, e.g. a sphere or oval, that passes just inside the sinal sphincter and holds the lumen in place, or a wire or tether from the lumen to the breast skin to be held with an adhesive or other temporary anchor. Other systems can be designed into the probe units that provide the same tethering or anchoring effect.

Figure 2:
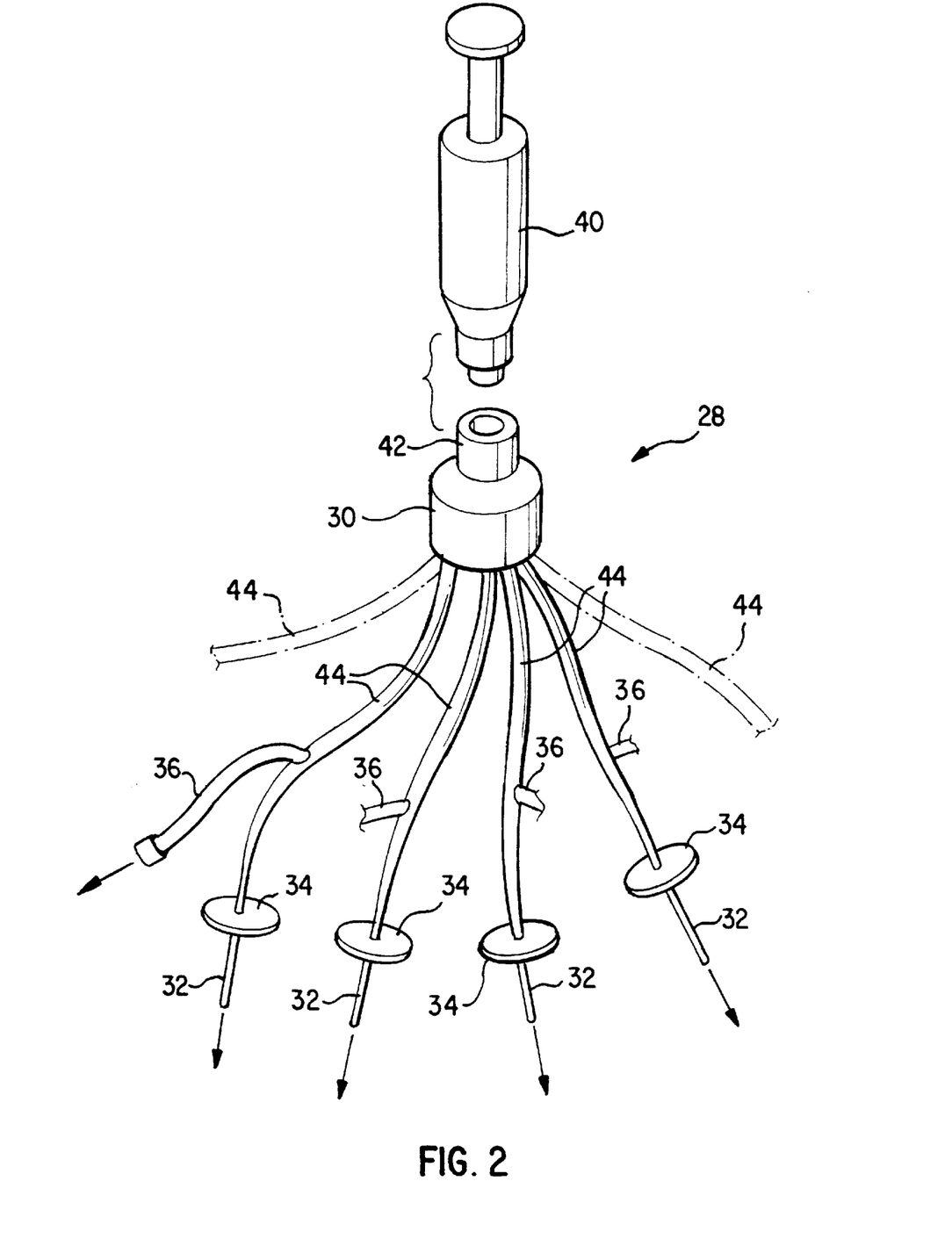
FIG. 2 shows a basic multiple duct infusion and collection apparatus.
Figure 2A:
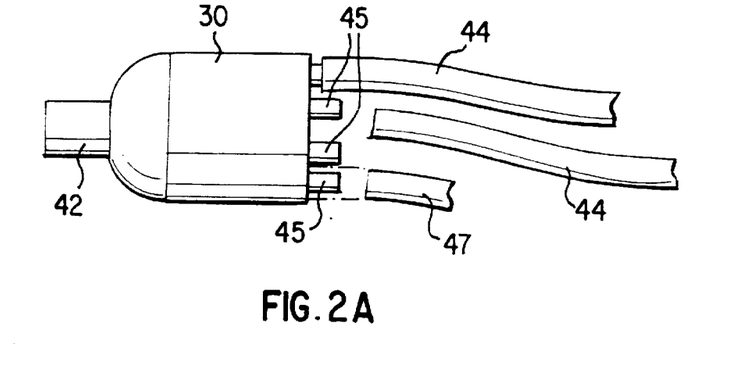

FIG. 2 illustrates a multiple duct infusion and collection apparatus 28 having a syringe 40 or other fluid infusion unit for placing fluid in an inlet 42 of a manifold 30. The syringe 40 or other fluid infusion unit can be preloaded with wash fluid or other agent for delivery to two or more ducts. Individual probes 44 are removably attachable to outlets 45 formed on the manifold 30. As described previously, this allows the user to connect a number of probes 44 equal to the number of ductal orifices to be accessed in the procedure. Those outlets 45 which are not used can be blocked, for example, by using a cover 47 which is placed over the outlet. Alternatively, valves could be provided in the manifold, or each of the outlets 45 could be covered by a breakable seal which is only opened if that outlet is to be connected to a probe 44.

Figures 2B, 2C, 2C:
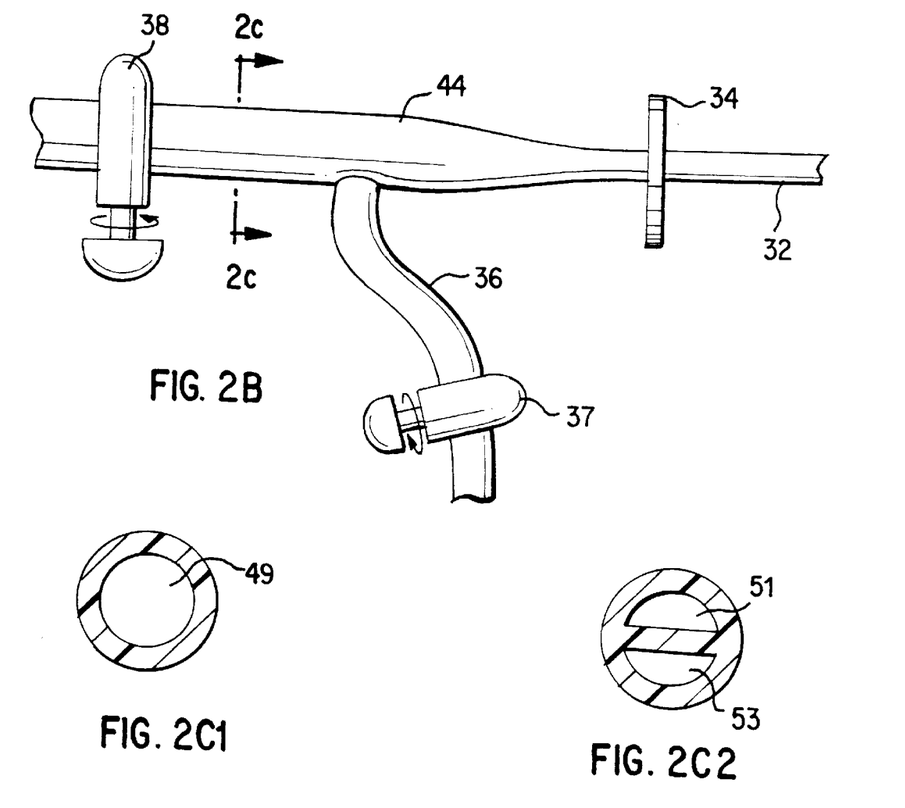

Referring to FIG. 2B, each probe 44 may be provided with a manually controllable valve 38 or other fluid control element, such as a one-way valve. The valve 38 will allow the user to selectively isolate individual probes 44 at a point between the syringe 40 and the breast. Such isolation is useful in at least two circumstances. First, if one or more probes 44 are not to be used, they may be simply turned off. Thus, to an extent, valve 38 is an alternative to valves or other sealing means which may be provided on the manifold 30. Additionally, the valve 38 may be used when it is desired to remove an infused fluid from the ductal network of the breast. In that case, the valves 38 would be closed, and fluid aspirated or otherwise collected through a collection tube 36 which is attached to a lumen of the probe 44 upstream of the valve, i.e. at a point between the valve and probe tip 32 which is introduced into the orifice of the ductal network. Optionally, the collection tube 36 may also include a valve 37 for isolating the collection tube from the lumen of probe 44. Usually, probe 44 will also include a stop plate or flange 34, as generally described in connection with FIG. 1.

The probes of the present invention will include at least a single lumen, where the lumen is used at least for introducing fluids into a plurality of ductal networks in a human breast, as described previously. Usually, the lumen(s) will also be used for aspirating and collecting fluids from the ductal networks. In the latter case, the lumen may be a single lumen 49, as illustrated in FIG. 2C1. Alternatively, the lumen could be divided into an infusion lumen 51 and aspiration lumen 53 as illustrated in FIG. 2C2. The use of a single and dual lumen devices is described in copending application Ser. No. 09/473,510, which has previously been incorporated herein by reference.

Figure 3:
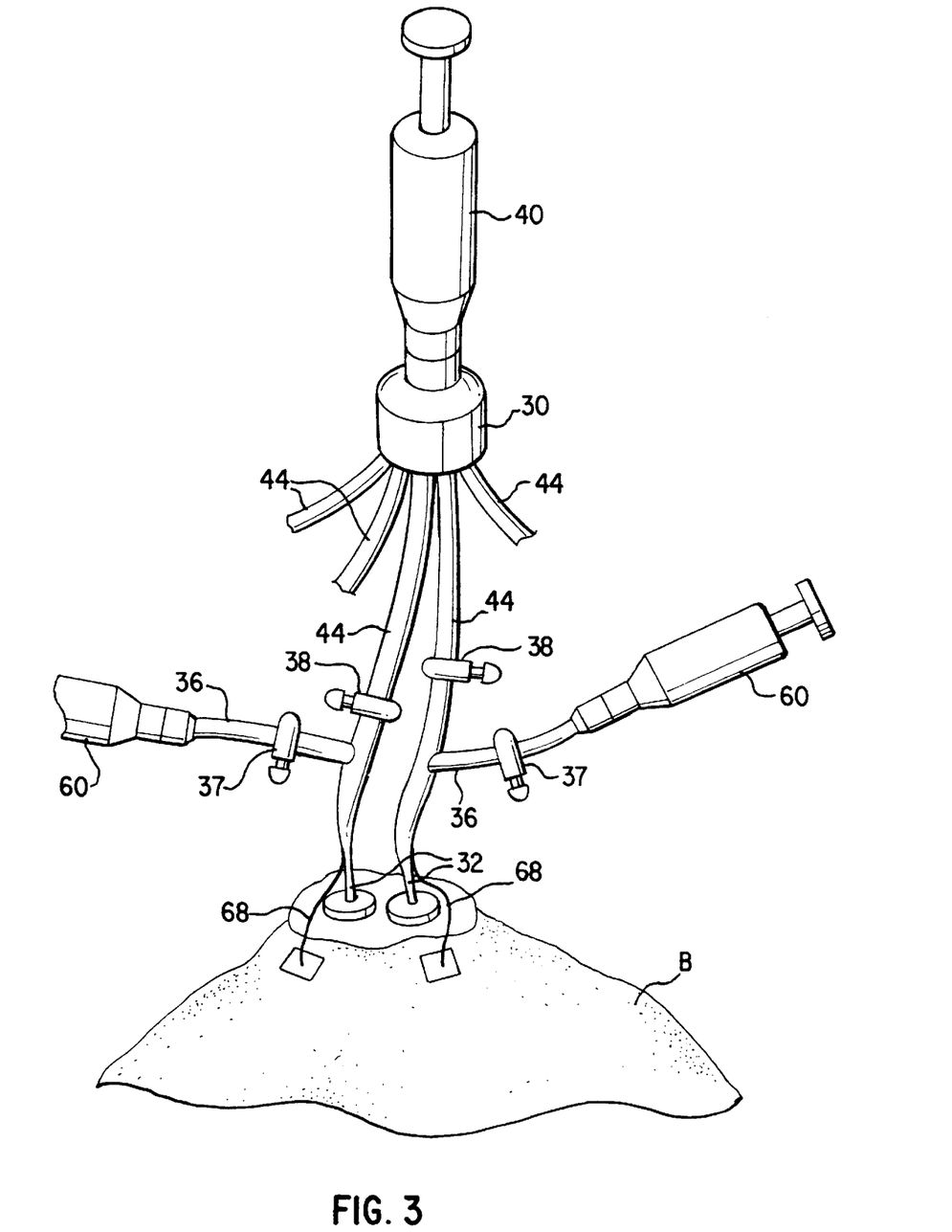
FIG. 3 shows a basic multiple duct infusion and collection apparatus accessing multiple breast ducts of a breast.

Referring now to FIG. 3, use of the ductal infusion and collection apparatus 28, described above, for delivering and collecting a wash or therapeutic fluid to a human breast B will be described. Tips 32 of probes 44 will be introduced through orifices of the individual ductal networks in the breast, as generally described in the prior copending applications which have been incorporated herein by reference. Although only two probes 44 are shown introduced to the breast B, it will be appreciated that a larger number of probes, usually up to the total number of orifices in any breasts (e.g. 12) may be simultaneously and/or sequentially introduced to the breast. Once the tips 32 of the probes 44 are introduced, they may be optionally anchored in place, e.g. using tethers 68 which are attached to adhesive pads or other anchors. Fluid may then be introduced into the multiple ductal networks simultaneously using a single syringe 40 or other fluid infusion unit, e.g. a pump. The fluid will be introduced in a volume and at a pressure selected depending on the purpose of the procedure. After the fluid has been introduced, the valves 38 may be closed in order to hold the fluid in the ductal networks and prevent backflow of the fluid from the networks into the manifold 30. Optionally, the breast B may be massaged at this point in order to distribute the fluid within the ductal networks. When it is desired to remove the fluid, individual valves 37 in the collection tubes 36 may be opened in order to permit flow from the ductal network to a collection device, such as syringe 60. The use of a syringe or other collection device having an aspiration capability is preferred, but not necessary since at least a portion of the fluid could be removed by simply allowing it to flow out and/or pressuring the breast to force the fluid out.

The subject apparatus have an inlet which can be made e.g. of a plastic or other material, e.g. preferably a disposable material that can be sterilized. The inlet can be rigid or flexible so long as it can accommodate an instrument that delivers the substance through the inlet. For example, the inlet can be cylindrical for receiving a syringe tip. In that case, the instrument to deliver the substance into the inlet can be, e.g. a syringe capable of being loaded with the substance and having a tip capable of accessing the inlet. The syringe can be a syringe adapted for use in this apparatus (e.g. without a hypodermic needle attached to the tip) as described in U.S. Pat. Nos. 5,308,331, 4,391,272, 4,775,364, 4,863,427, 4,929,231, 4,932,941, and U.S. Pat. No. 4,950,243, which describe disposable single-use syringes. The syringe or delivery instrument may also be reusable. The syringe may be adapted from the pre-filled syringe described in U.S. Pat. No. 4,878,903. The adaptations can comprise that the syringe accesses the inlet having access to two or more outlets and/or probe lumens that are capable of accessing a breast duct. The access and connection between the instrument to deliver the substance and the inlet can comprise a nested fit configuration of a syringe tip into the inlet, or a connection comprising threads on the inside or outside of the inlet and/or on the inside or outside of the syringe tip so that the syringe tip and the inlet can be attached to each other by screwing one into the other. Other connections such as a snap connection, for example, or any other way to fit a delivery instrument into an inlet can be used.

Instruments other than a syringe can be used to deliver the substance into the inlet, particularly depending on the volume of substance to be delivered, and the consistency of the substance. For example, an instrument having a piston or other method of pushing a substance into the inlet can be used. A volume of liquid can be delivered, for example from a bag having a tube connectable or accessible to the inlet, and delivery of the substance can occur by placing the bag above the inlet and opening the tube access so that the liquid can flow into the inlet by gravity. The flow of the substance into the inlet in this case can be controlled by a stopcock or other such on/off regulating mechanism, including the potential to lower and raise the rate of flow to achieve a slow, intermediate, or high rate of delivery. The advantage of a syringe used as the delivery instrument is that it can provide a necessary pressure on the substance as it passes into the inlet for delivery to the ducts, and that applied pressure can be calibrated and controlled by pushing the syringe plunger at a certain rate or with a certain force.

Whatever the delivery instrument that is used, preferably the delivery instrument is calibrated and the pressure that can be applied from the instrument is quantifiable and preferably also the pressure is controllable so that a faster or slower rate of flow can be generated as needed for the particular delivery purpose. For example, as described below the lavage embodiment of the delivery apparatus requires that the flow be controllable from at least the inlet of the apparatus, and possibly also from outflow lumens as well.

The inlet is connected to two or more inflow lumen or probe lumens. Thus, in a simple embodiment, an inlet is connected to two inflow lumens and the substance passes through the inlet into each of the two inflow lumens. A typical human breast has from 6 to 12 milk ducts on average, and thus 6 to 12 ductal orifices. In a procedure involving diagnostic analysis of the breast by analyzing the breast duct fluid and cells it is desirable to access all of the breast ducts in the breast. This access can be accomplished at the same time or virtually simultaneously using the apparatus of the invention (i.e. using the same procedure as opposed to multiple procedures).

In addition, the apparatus provides an opportunity to minimize the tissue stress to the patient where the steps of massaging and squeezing are applied to the breast, e.g. in a lavage procedure. Using the apparatus allows approximate simultaneous access and approximate simultaneous delivery of the lavage agent to the accessed ducts; thereafter and during the infusion of lavage fluid the practitioner can massage and/or squeeze the breast, affecting the fluid and cell yield of all the accessed ducts in the same massaging and/or squeezing action, and thereby cutting down the amount of massaging and/or squeezing of the breast required for the entire procedure. Massaging and/or squeezing of a breast having ducts accessed in a duct-by-duct fashion, requires multiple massaging and/or squeezing applications to the breast, and risks the inevitable increased discomfort to the patient and potential damage to the breast tissue by repeated handling.

In order to construct a generic apparatus capable of use by all patients, a inlet is connected to a plurality of outlets which can each connect to an inflow lumen or probe lumen. The amount of inflow lumens required should be at least more than 3, or around 6 or more, or typically about 12. Thus the apparatus can comprise about 6 to about 12 or more outlets and a one-to-one option of corresponding connectable inflow lumens (and also, perhaps, having additional inflow lumens, or options to add additional inflow lumens) so that the total potentially usable lumens or outlets in the apparatus are in a range of from about 12 to about 16 in order to cover the rare individual who has more milk ducts than the norm. However, not all outlets need to communicate with a breast duct (in any given procedure), and those outlets and/or inflow lumens not in use can be capped or blocked. Thus an embodiment of the apparatus is an inlet connected to exactly the number of operable outlets and inflow lumens as the patient has breast ducts, and which it is desirable to access, while unused outlets remain capped or blocked from delivering the substance or connecting to a probe or inflow lumen, although possibly still capable of communication with the inlet. Another embodiment of the apparatus is an inlet connected to exactly the number of outlets and/or inflow lumens as the patient has breast ducts that require therapeutic treatment or access for other purpose, while the unused outlets remain capped or blocked from delivering the therapeutic substance. For example, a patient having 3 affected ducts will have the inlet operably connected to 3 outlets and 3 inflow or probe lumens, and each of those inflow lumens will access an affected duct.

The connection between the inlet and the outlets can be removable. The removable connections can include a member to control a flow of the substance, for example a stopcock or valve. The removable connections can also include a cap to block connection with an inflow lumen. This latter embodiment is useful when the apparatus or manifold has more connections to inflow lumens than the patient has ducts on her breast, e.g. where the manifold has 12 connections and the patient has 10 ducts, two outlet connections may be capped to prevent passage of the substance. The other 10 connections can be connected to inflow lumens that access each of the 10 ducts.

The connection between the inlet and the inflow lumens and/or the outlets can be of molded plastic or other polymers, including e.g. resilient, rigid or flexible materials. Multiple lumens together may form a manifold having a inlet and multiple branching lumens. Between the inlet and the inflow lumens can be a volume of a very small capacity or a volume of larger capacity for holding the substance as it is dispersed to the various inflow lumens. Thus the volume between the inlet and the inflow lumens can be e.g. a cylinder, a disk, a bulb, or an amorphous shape that expands with the introduction of fluid. The requirements of this intermediate volume and its shape may be dictated by such parameters e.g. as the desired pressure of delivery of the substance, and the viscosity of the substance, and other parameters as well including, e.g. optimal shapes for handling, use, and attachment of inflow lumens. For example the needs for the volume in a lavage procedure may vary from those of simple delivery of an agent to the ducts.

The distal end of each inflow lumen operably connected to the inlet and manifold at the outlets accesses a breast milk duct through a ductal orifice. Thus, e.g. where two ducts are accessed, two inflow lumens are connected to the inlet each at an outlet; where all the ducts on a given nipple are accessed, e.g. where the particular breast being accessed has 8 ducts, then 8 inflow lumens are operably connected to the inlet for delivery of a substance to the 8 accessed ducts.

The inflow or probe lumens can be any lumen capable of transferring a substance to the breast duct. Thus, for example, catheters and cannulas may be inflow or probe lumens. The lumen may have multiple segments, e.g. a flexible lumen for extending flexibly to its corresponding outlet, and a rigid lumen at the distal end where ductal access occurs, the rigidity facilitating in part the access to the duct through the orifice. The multiple segments, e.g. the flexible and rigid portions may be permanently connected or removable. Catheters for delivery or lavage can have features essentially as available e.g. as described in the following patents: U.S. Pat. Nos. 5,279,551, 4,957,484, 5,827,237, 5,810,867, 5,810,789, 5,807,329, 5,797,869, 5,795,326, 4,795,424, 5,702,365, 5,683,640, 5,649,909, 5,637,102, 5,599,324, 5,364,344, 5,350,358, 5,333,609, 4,682,978, and U.S. Pat. No. 5,207,648. Also patent application Ser. No. 09/473,510, filed Dec. 28, 1999 (copending and co-owned with the present application) describes useful catheter features and elements that can be incorporated into the present apparatus to useful effect.

A duct probe inserted into the ducts to dilate the ducts can accomplish access of the ducts. In the past, ductal access has generally been accomplished by placing galactography needles or dilators of increasing sizes into the ductal orifice to dilate the orifice to a diameter sufficient to accept the subject lumen. The state of the art has been to place a small galactography needle or dilator into the duct, remove it, replace it with an incrementally larger needle or dilator, remove that, and replace it with a still larger needle or dilator, and so on. Eventually the needle or dilator occupying the orifice is the same size or just larger than the subject lumen. That needle is removed and replaced by the lumen of a catheter or cannula or other like tube and the procedure can continue from there.

Instead of using multiple needles or dilators of ascending size, a duct probe that is a separate single graduated unit can be used. The duct probe can be replaced by the inflow lumen once the duct is sufficiently dilated, or the duct probe can be a unit that is connected to the inflow lumen. Where the unit is connected to the inflow lumen, the duct probe can be a cannula-like member essentially constructed as described in U.S. Pat. No. 5,593,393, with adaptations and adjustments to probe and dilate a breast duct rather than a lacrimal duct, and the cannula can be connectable to an inflow lumen that is connected to the inlet. Thus, the apparatus may comprise inflow lumens capable of accessing, dilating and delivering a substance to the breast duct with a single entry. Alternatively, the pre-dilation may be accomplished with a separate tool, e.g. successively larger galactography needles or a single graduated duct probe, or may be accomplished by a tool integral to the inflow lumen, having itself a lumen for delivering the substance. Where the lumen then accesses the duct, the tip of the lumen is designed for such access, e.g. as described in U.S. Pat. No. 4,543,087. The access member or duct probe, whether separate from or attached to the inflow lumen, can be modified from basic needle designs available from companies that provide such medical tools, e.g. Ranfac Corporation located in Massachusetts (phone 888-821-0098), Medical Device Technologies, Inc. located in Gainesville, Fla. (phone 352-338-0440), and Cook, located in Bloomington, Ind. (phone 800-545-0890). In any event, whether the duct probe is connected to the catheter lumen or whether the duct probe is removable or separate from that lumen, its dimensions can be dictated primarily by the goals of dilation of the orifice, namely that the tip must be able to access an undilated ductal orifice, and its graduated portions must be expanded or expansive to a point that dilates the duct to a point that provides either comfortable delivery from an inflow lumen attached to the probe or comfortable and easy access by the inflow lumen (as the probe is replaced). For a discussion generally of some of the differences in catheter design and how the design can affect resulting function see Walters et al, (1997) Int J. Artif Organs 20(4):208–12.

The probe or lumen can be made of a rigid material and can be graduated, being narrow at a distal end that accesses the duct first, and expanded at a proximal end capable of contacting a catheter or extending outside the duct. The fact that the probe is graduated provides a means to dilate the opening at the ductal orifice for allowing access of a catheter or other inflow lumen for delivery of a substance. The probe can be a solid member, or the probe can be a tube having a hollow portion allowing fluid flow. The probe can have more than one lumen, e.g. a dual lumen probe.

The probe can further comprise a means for anchoring the member so that the access member does not slide out of the duct. The attachment means can comprise any system that anchors or fixes the access member into the duct during the delivery or lavage procedure. Thus, fasteners can be constructed that are integral (e.g. welded or molded to) the probe or access member. The fastener can be anything that allows attachment of a tether to the probe, e.g. the fastener can be a hook, an eye, a region of ridges on the probe, or other means capable holding a tether at a fixed point or region on the access member. A tether is then attached to the fastener for tethering the member accessing a duct to the breast and essentially also to the duct. When the probe is accessing the duct, the fastener will be optimally located about even with or just above the nipple surface. The tether that attaches to the fastener portion of the probe can be anything that can attach at that point and be comfortably and securely affixed to the skin of the breast for anchoring the probe in the duct. Thus, the tether can be a string, line, wire or tape, for example. The tether is affixed to the skin of the breast by a suitable, removable means, e.g. a tape that can adhere to skin. Attachment means on the probe can include e.g. a hook or an eye (the hook or eye being tethered to the breast or other anchor). The probe may also be designed to have modalities that cause the access member to stay in the duct without tethering the member to the breast. Thus, e.g. the probe or access member can have ridges located below the ductal orifice, small non-puncturing barbs located below the ductal orifice, or perhaps a widened region of the accessing lumen located below the ductal orifice, optionally with some striations or a rough region that can grab the ductal lumen near the orifice and retain the access lumen in the duct during the delivery procedure. A knob can be placed on the probe that passes through the lactal sphincter and hugs the lumen once at that position. The ridges, rounded barbs, or striated and/or widened region may serve to keep the lumen inside the duct without the need to actually tether the access tool to the breast. Ridges can be placed on the lumen at the region below the orifice, or above the orifice for attaching a tether. Where a line or other tether is tied to the fastener, the fastener can be located e.g. about 2–3 centimeters from the distal tip, or in the range of from about 1 centimeter to about 8 centimeters from the distal tip. When the probe has accessed the duct, the fastener holding the tether is approximately flush with the nipple surface and at the ductal orifice. In the tether embodiment, the tether can be affixed to the skin (of the breast) e.g. by tape or other adhesive to anchor each probe to the accessed duct and prevent the probe or any attached catheter from sliding out of the duct during a procedure.

The means for anchoring the probes or access members that access the milk ducts can also comprise a plate having holes for containing the access lumens and a slidable ring or seal at each hole that allow the plate to be pushed to the nipple surface once all the target ducts have been accessed, thus holding the lumens in place because the lumens are anchored into the plate (e.g. by the ring or seal), and the plate once placed at the nipple surface remains there. Optionally, the plate can be anchored to the nipple surface, e.g. by a few tethers located on the plate and the tether can then be affixed by some adhesive means (e.g. tape) elsewhere to the skin of the breast. The plate can have multiple holes so that the plate can accommodate a various number of access lumens at various locations on a given nipple surface. Thus the plate is typically constructed to meet the generic needs of any patient having a lavage procedure by a apparatus capable of accessing of more than one milk duct at the same time, taking into account that the number of ducts accessed and their locations vary from patient to patient and with various contexts for the lavage or delivery procedure.

The apparatus for delivering a substance to the breast ducts can further comprise a separate collection lumen branching from the probe lumen for collecting the fluid delivered to the ducts, mixed with other ductal contents including fluid, cells and other elements in a breast duct, e.g. for use in a lavage procedure. The collection is positioned so as to divert fluid back flow from the duct to the collection receptacle and prevent flow back into the main chamber of the manifold. A control valve can be placed in the probe lumen above the collection lumen to control back fluid flow. The collection lumen can further comprise a collection receptacle at its distal end for collecting the fluid that comes from the duct diverted through to the collection lumen. For example in the case of a lavage procedure, the inflow or infusion lumen will deliver the lavage or wash fluid into a duct, and the collection lumen will retrieve some of this fluid mixed with ductal fluid that can be collected in the collection receptacle at the distal end of the collection lumen. Each duct can have a separate collection receptacle at the distal end of its collection lumen. These receptacles can be labeled to correspond to the duct. Such a collection procedure provides the practitioner with fluid and cell samples from each accessed duct so that analysis can be made of each duct separately, and a disease condition when detected is localized to a specific duct. Multiple fractions may be collected from a given outflow lumen into separate collection tubes.

In the case of using the apparatus for a lavage procedure of the ducts of a breast, other features can be added to the apparatus. For example, each collection lumen can be connected to a syringe or other receptacle or mechanism capable of providing a vacuum and/or also receiving the fluid and cells. Thus, when a syringe delivers a lavage fluid through the inlet to the inflow lumens and to the ducts, the collection syringes connected to distal ends of the collection lumens can be pulled back to increase the yield of wash fluid containing ductal fluid and cells by creating a vacuum pressure. During this modified lavage procedure using vacuum pressure at the collection lumens, the inflow pressure and the outflow pressures can be adjusted and adjustable to fit the particular needs of the procedure while it is on going. For example, the inflow rate can be increased in the beginning of the procedure to ensure that as much fluid is delivered to the accessed ducts as possible. Also be example, once the ducts have been filled, the outflow negative pressure may be applied to the outflow lumens to encourage the fluid filling the ducts to leave the ducts through the outflow lumens.

The fluid infusion syringe and the collection syringes (or other delivery and/or suction mechanisms) can be connected so that these reciprocal pressures can communicate, e.g. where the inflow pressure increases, the various outflow pressures of the various accessed ducts will also increase. Generally the pressures of the collection syringes need to be monitored so that they do not exceed a limit that would cause an accessed duct to collapse, which limit is dependent on such parameters as e.g. the amount of fluid in the duct or ducts, the number of accessed ducts and the fluid inflow rate from inlet and in the inflow or probe lumens.

Substances that can be delivered to the breast milk ducts include any substance a practitioner might desire to deliver to a breast duct. Such substances can include, e.g. a lavage fluid for washing the ducts, a diagnostic agent, a prophylactic agent, a therapeutic agent, or an agent to occupy space in a duct.

The lavage fluid can be delivered to the ducts for the purpose of collecting ductal fluid mixed with lavage fluid. The retrieved mixture of wash and ductal fluid may also contains ductal epithelial cells and other ductal and cellular components (e.g. including molecular species) that can provide the basis of an analysis of the condition of the breast milk ducts. Lavage fluid can be a saline solution, e.g. normal saline, or phosphate buffered saline (PBS), or other fluid capable and suitable for washing a body duct. The lavage fluid will generally be biocompatible and nontoxic to the patient. The lavage fluid can further comprise additives to facilitate the lavage of the duct, e.g. agents disclosed in U.S. Ser. No. 60/114,048 filed Dec. 28, 1998, which are incorporated by reference in their entirety.

The substance delivered to the accessed breast ducts can be a diagnostic agent. Such an agent can diagnose a condition including a cancer or precancer condition, including atypical ductal hyperplasia (ADH) and low grade ductal carcinoma in situ (LG-DCIS). The agent may also have the ability to diagnose other breast related conditions, including, e.g. fibrotic, cyst or conditions relating to lactation. Diagnostic agents can include targeting diagnostic and therapeutic agents disclosed in U.S. Ser. No. 60/102,829 filed Oct. 2, 1998 and U.S. Ser. No. 09/410,336, filed Oct. 1, 1999 herein incorporated by reference in their entirety.

See co-owned and co-pending U.S. Ser. No. 09/473,510, filed Dec. 28, 1999 and PCT application no. 99/31086, filed Dec. 27, 1999 both for descriptions of other agents (diagnostic, therapeutic and/or prophylactic) deliverable to the ducts using the apparatus, methods and kits. The substance delivered to the ducts can be a prophylactic or therapeutic agent including, e.g. a cytotoxic, cytostatic, apoptotic or differentiating agent. Some such agents are listed in U.S. Pat. No. 5,763,415 and WO 97/05898 both to Sukumar. Other agents include, e.g. estrogen activity modulators as described in co-owned and co-pending application U.S. Ser. No. 09/313,463 filed May 17, 1999, herein incorporated by reference in its entirety.

A substance delivered to the duct to occupy space in the duct can be a gel or liquid that can convert into a gel once inside the duct, or a material that can fill the duct for accomplishing such purpose as having the duct easily identifiable for a medical procedure. See co-owned and co-pending applications U.S. Ser. No. 60/138,693 filed Jun. 11, 1999, herein incorporated by reference in its entirety.

A method of delivery of a substance to two or more ductal networks in a breast is provided. Access is established to two or more ductal networks in the breast through a ductal orifice of each ductal network. Thereafter a substance is delivered to and/or a fluid is collected from two or more of the ductal networks. Establishing access can comprise inserting an access probe in each ductal orifice to be accessed. At least some of the access probes can be fluidly connected by a manifold so that substance may be delivered simultaneously to the connected probes through the manifold. Thus, all of the access probes can be fluidly connected to the manifold so that fluid may be delivered simultaneously to all probes. By the method, the substance can be delivered simultaneously to all of the accessed ductal networks. Fluid can be collected in separate receptacles for each ductal network. Access can be established to each of the ductal networks in a breast, so that all the ducts on a breast are accessed and the agent is delivered to all of the ducts.

A method for delivering a fluid to two or more ductal networks in a breast comprises locating two or more ductal networks in a nipple of the breast, inserting an access probe through an orifice of each of the located ductal networks; and infusing the fluid through a manifold to each of the probes. The method can further comprise connecting individual probes to the manifold so that the number of probes connected to the manifold is the same as the number of probes inserted into ductal orifices. The method can further comprise providing an assembly of a number of access probes greater than the number of ductal orifices. The access probes can be attached to the manifold before or after accessing their respective ducts. The probes can be preloaded with a substance and placed or attached to the manifold. Those access probes connected to the manifold can be selectively blocked which are not inserted to a ductal network. Thus, the system can provide for accessing as few or as many of ductal networks desired, and for filling those ducts with a substance, and/or retrieving from those ducts a fluid sample. The method can further comprise collecting fluid from each accessed ductal network, wherein the fluid is collected separately so that no one fluid from a ductal network is mixed with fluid from another ductal network.

The invention also contemplates methods of accessing two or more breast ducts for delivery of a substance. The substance can include e.g. therapeutic, diagnostic or prophylactic substances, or delivery of a lavage fluid and conducting a lavage procedure of the breast ducts. Lavage procedures include delivering a substance for washing the duct (e.g. a lavage fluid) and retrieving or collecting that lavage fluid, albeit mixed with ductal fluid containing ductal cells and other ductal contents. Lavage procedures can include delivery of the lavage fluid with additives, or delivery of other agents before, after or during delivery of the lavage fluid.

The methods of accessing more than one breast duct occur using the apparatus of the invention such that all the ducts that the practitioner desires to access are accessed and the substance delivered (and/or collected in the case of a lavage procedure) at approximately the same time, i.e. in the same procedure or simultaneously. Such simultaneous access results in the timesaving and efficiency benefits of the invention. Delivery and subsequent fluid collection (where applicable to the procedure) are achieved once all the ducts that the practitioner desires to deliver a substance to have been accessed. Access occurs using a duct probe and/or lumen (e.g. a probe, catheter, cannula or the like). After all the ducts are accessed, the delivery and/or collection can be implemented. With regard to the simultaneous nature of the methods it is understood that because the apparatus used in the methods provides a infusion inlet for the substance to be delivered, and provides for access of more than one breast duct at the same time, that the delivery of the substance to the ducts occurs at the same time, or at about the same time. It is understood that during the delivery procedure adjustments can be made in order to ensure that the delivery of a substance occurs in all the ducts about at the same time. Thus, e.g. e.g. a small duct may fill up faster than a larger duct, or where a particular duct may require adjustments of the duct probe accessing it so that fluid flow can be maintained, but with for all practical purposes the delivery to all the ducts occurs at the same time, using a single apparatus having at least more than one access lumen, delivering a substance to all accessed ducts by a inlet.

As the methods of the invention require that the ducts to be accessed are accessed at about the same time, in the same procedure, thus, e.g. duct 1 is accessed by the duct probe, followed by duct 2, etc. until all the ducts are accessed by a duct probe connected to an inflow lumen or an inflow lumen itself. The inflow lumens are connected to the inlet at the outlets of the manifold. The lumens may be pre-primed or primed after connection with the manifold. At that point simultaneous delivery of the substance can occur by applying pressure to the syringe or other delivery instrument that contacts the inlet. The substance flows into the inflow lumens through them to the accessed ducts. It is expected, anatomy of the human breast invariably dictating that not all ducts of the breast are exactly the same size or of the same capacity, that some ducts may fill faster or slower than other ducts. With regulated and controlled and carefully monitored inflow pressure, however, the practitioner can adjust, control and monitor the inflow of the substance, and observe each of the accessed ducts for whether delivery of the substance is occurring and whether the collection from the duct (in the case of lavage) is optimal and sufficient.

The process of delivering a substance to more than one breast duct requires connecting the apparatus described above (having an inlet connected at individual outlets to more than one probe lumen each capable of accessing a breast milk duct) to a breast. For example, where the breast has 7 ducts and the practitioner desires to access all of them, the apparatus for accessing those ducts will have 7 outlets to open probe lumens capable of accessing those 7 ducts. Unused lumens that are part of the apparatus can be capped or closed off. Once the lumens have accessed the ducts, the substance can be delivered, e.g. by syringe through the inlet of the manifold and out the outlets to the probe lumens and to the ducts. Identification of the ductal orifices for accessing them with a probe or other tool can be accomplished by a variety of means, including e.g. a characteristic electrical signal at the nipple surface to indicate an orifice (see e.g. co-owned application attorney docket 00-042 filed Jan. 12, 2000) injecting or contacting the nipple with a dye or other substance that can be extruded from the orifices thereby identifying their location (see 08/931,786 filed Sep. 16, 1997 and 09/153,564 filed Sep. 15, 1998), or other practical or suitable means. Corresponding to these identification means, the practitioner may also want to dekeratinize the nipple surface (including most importantly removing the keratin plugs from the ductal orifices) by means of applying a dekeratinizing agent (e.g. acetic acid, empigen, or cerumenex; the nipple can be dekeratinized with 5%–50% acetic acid to remove keratin and other potentially blocking and contaminating substances from the ductal orifices) or by using a forceps to remove visually detectable plugs. Where it is desirable and important to identify and access all the ducts on the nipple surface, e.g. where a diagnostic procedure (e.g. a lavage) is being conducted, a practitioner will take care in being thorough with such identification and take care to access all identified ducts, and possibly take the time to double-check with a parallel or complementary identification procedures so that no ducts are missed.

As described for the apparatus embodiments, accessing the ducts can be accomplished either by the inflow or infusion lumen (e.g. a catheter or cannula) directly, or the duct can first be accessed by a needle or probe that dilates the duct and provides sufficient opening for the catheter or other lumen to enter the duct. Where the orifice is accessed by a catheter having a modified tip being at least more rigid than the catheter or lumen and having a graduated diameter for dilating the duct so that the substance flowing through the lumen can enter the duct, the rigid tip can have a hook or an eye or some other such means to attach a line (to the skin of the breast) to keep the probe from sliding out of the duct. Where the duct probe is attached to the catheter, the probe can have a lumen so that the substance is delivered to the duct from the catheter lumen into the probe lumen and into the duct. The attached probe can be graduated to dilate the duct so that the duct can accommodate a lumen of sufficient diameter to efficiently deliver a substance. Where a separate probe is used to access and dilate the duct in preparation for catheter access, the probe can be a solid member, having graduated diameter for dilating the duct. After the dilation is complete the dilator is removed and replaced with a catheter tip or other inflow lumen.

The methods of the invention include methods of ravaging more than one milk duct at the same time by connecting a apparatus to the breast that has an inlet connected to two or more outlets that each connect to a probe or lumen capable of accessing a breast duct. The distal end of the probe lumens can access a milk duct through a ductal orifice. The apparatus may also include a collection receptacle off the probe lumen to collect any fluid flowing out from or retrievable out from the duct.

An advantage of the methods of the invention providing simultaneous access of the breast ducts and retrieval of ductal fluid and cellular material is that the added steps of massaging and squeezing need only be done once for all the accessed ducts, thus limiting any patient discomfort or minimizing any potential tissue damage to the breast tissue, but requiring that a cycle of massaging and squeezing need only be conducted once per procedure per breast.

A kit for delivering a substance to a two or more of ductal networks in a breast is provided, having two or more of probes each having a lumen and being configured for introduction into a ductal network of the breast, and instructions for use setting forth a method according to those described and exemplified herein. A kit can comprise a manifold having an inlet and at least twelve outlets, and at least twelve access probes connectable to the outlets on the manifold, wherein the access probes are configured for insertion through an orifice of a ductal network of a breast. The kit can further comprise a separate collection receptacle for each probe.

Kits for use by a practitioner or patient can comprise the apparatus described herein, along with instructions for use of the apparatus. The kits can further comprise attachable or attached inflow lumens (e.g. catheters), duct probes (e.g. a graduated duct probe), and/or catheters with connected duct probes at their distal ends. The catheter may have the graduated duct probe attached to it at the distal end for accessing the duct. The graduated duct probe can have an anchoring member such as describe herein for attaching the probe (or other access member) and its attached catheter into the duct and preventing it from sliding out. Where the probe is unattached to the catheter, and is used for dilating the orifice, the catheter will have a tip appropriate for accessing the dilated duct upon removal of the probe (or probes). The kit can also include appropriate reagents e.g. wash agents, dekeratinizing agents, and ductal orifice identifying agents. The kit may also contain the substance for delivery, e.g. a wash fluid for performing a lavage, or a diagnostic agent, prophylactic or therapeutic agent for delivery, or an agent for occupying space in the duct.

The kit may also contain fluid additives or other agents to be administered to the duct in order to facilitate some part of the procedure. The kit can also have vessels, e.g. collection tubes for collecting lavage and ductal fluid from an outflow lumen. These collection tubes can contain substances that anticipate analysis of the collection fluid, including, e.g. preservative in the tubes. Any kit will contain complete directions for use of the items supplied in the kit for performing the delivery or lavage procedure desired by the kit user.

The following table illustrates results obtainable from a lavage procedure of the right and left breast of a patient undergoing a diagnostic lavage procedure to identify whether a cancer or pre-cancer condition exists in any of the ducts of the patient. Single lavage procedures are conducted for the right breast having 7 ducts and the left breast having 9 ducts

TABLE 1

| Breast/Duct | Lavage Fluid Delivered | Fluid Collected | Cells Collected | Diagnosis (cytology) |
|---|---|---|---|---|
| R-1 | PBS-20 ml | ++++++ | ++++ | scattered clusters of benign unremarkable ductal cells |
| R-2 | PBS-20 ml | +++++++ | +++++ | ADH: some ductal cells exhibiting cytological characteristics of atypical ductal hyperplasia |
| R-3 | PBS-20 ml | ++++ | ++ | scattered clusters of benign unremarkable ductal cells |
| R-4 | PBS-20 ml | +++++ | +++ | scattered clusters of benign unremarkable ductal cells |
| R-5 | PBS-20 ml | +++ | + | Hyperplasia: some ductal cells exhibiting cytological characteristics of ductal hyperplasia without atypia |
| R-6 | PBS-20 ml | +++++++ | +++++ | ADH: some ductal cells exhibiting cytological characteristics of atypical ductal hyperplasia |
| R-7 | PBS-20 ml | ++++++ | +++ | scattered clusters of benign unremarkable ductal cells |
| L-1 | PBS-20 ml | ++++ | + | scattered clusters of benign unremarkable ductal cells |
| L-2 | PBS-20 ml | +++++ | ++ | scattered clusters of benign unremarkable ductal cells |
| L-3 | PBS-20 ml | +++++ | ++++ | ADH: some ductal cells exhibiting cytological characteristics of atypical ductal hyperplasia |
| L-4 | PBS-20 ml | ++++++ | ++++ | ADH: some ductal cells exhibiting cytological characteristics of atypical ductal hyperplasia |
| L-5 | PBS-20 ml | +++++++ | +++++ | ADH: some ductal cells exhibiting cytological characteristics of atypical ductal hyperplasia |
| L-6 | PBS-20 ml | ++++ | ++ | scattered clusters of benign unremarkable ductal cells |
| L-7 | PBS-20 ml | +++ | + | scattered clusters of benign unremarkable ductal cells |
| L-8 | PBS-20 ml | +++++ | +++ | Hyperplasia: some ductal cells exhibiting cytological characteristics of ductal hyperplasia without atypia |
| L-9 | PBS-20 ml | ++++ | ++ | Hyperplasia: some ductal cells exhibiting cytological characteristics of ductal hyperplasia without atypia |

Table 2 represents a hypothetical treatment protocol of the hypothetical patient tested in Table 1. During each drug administration, the right breast ducts are accessed at the same time (R-2 and R-6) and the left breast ducts are accessed in a separated procedure also at the same time (L-3, L-4, L-5).

TABLE 2

| Breast/Duct | Drug | Dosage | Frequency of Administration | Repeat diagnosis by lavage |
|---|---|---|---|---|
| R-2 | tamoxifen | 10 mg/in time releasing gel | one weekly | every 3 months |
| R-6 | tamoxifen | 10 mg/in time releasing gel | one weekly | every 3 months |
| L-3 | tamoxifen | 10 mg/in time releasing gel | one weekly | every 3 months |
| L-4 | tamoxifen | 10 mg/in time releasing gel | one weekly | every 3 months |
| L-5 | tamoxifen | 10 mg/in time releasing gel | one weekly | every 3 months |

EXAMPLES

1. Cell Collection of Milk Duct Lavage of a Human Patient

The ducts of the right breast of a patient are identified by a characteristic electrical signal and as the nipple surface is probed with an electrode, areas of low electrical impedance (see co-owned and co-pending application attorney docket 00-042 filed Jan. 12, 2000 for details) are accessed with a duct probe attached to a dual lumen catheter. The electrode may be a probe capable also of accessing and dilating a duct that indicates a spot of low impedance. As such once the identification, access and dilation by the probe are accomplished the probe can be replaced by an appropriate lumen, e.g. a dual lumen catheter. Areas of high impedance are dekeratinized by application of acetic acid mixed with Velvacrol (50% v/w), a pharmaceutical vehicle comprising an aqueous mixture of petrolatum/mineral oil, acetyl alcohol, sodium laurel sulfate, cholesterol, methylparaben, butylparaben, and propylparaben. To keep the acetic acid in solution, methyl cellulose (100 mg) is pre-added to the Velvacrol (5 g). The mixture possesses a uniform pasty consistency and is applied to the nipple as an ointment or paste. The keratinolytic agent is typically left on the nipple for 24 hours or longer to remove the keratin plugs from the ductal orifices. The identified orifices are then accessed with a duct probe. Once a duct has been accessed, the probe is anchored into the duct by attaching a line to the probe at an eye (or loop) on the probe. The line is then affixed to the breast skin with an adhesive bandage that holds a line that is connected to the probe. The loop rests at about the nipple surface. Once all the ducts are accessed the area of the nipple surface thoroughly re-probed with the electrode to determine that all the ducts on that breast have been identified and that none have been missed. The patient has 10 ducts on the right breast. Collection tubes connected to the 10 outflow lumens have preservative in them.

A lavage fluid of 200 ml normal saline is inserted into a syringe that connects to the inlet of the connected apparatus. The syringe capacity is 250 ml. The plunger of the syringe is pushed to the 150 mark at a steady rate and the status of the duct probes, dual lumens and ductal orifices is carefully observed. Fluid is collected in separate collection tubes connected to the lumens. The breast is then massaged and squeezed gently from the base to the areola. The syringe at the inlet is pushed to 100 ml and the breast is squeezed and massaged at the same time. This second fraction is collected in new collection tubes and labeled accordingly. The breast is squeezed and massaged again. Another 50 ml is pushed out from the syringe, meanwhile the breast is squeezed and massaged and a third fraction collected. A fourth aliquot of 50 ml is delivered, and the breast also squeezed and massaged as the fourth fraction is collected.

A portion of fluid from each of the 4 fractions from each of the 10 ducts is transferred to a new tube and the cells spun down. The resulting cells are analyzed by cytology.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for lavaging two or more ductal networks in a breast, said method comprising:
   establishing access to two or more ductal networks in the breast through a ductal orifice of each of said respective ductal networks;
   simultaneously delivering a substance to two or more of the ductal networks; and
   collecting a ductal fluid sample from the two or more ductal networks using a plurality of indwelling probes.

2. A method as in claim 1, wherein said indwelling probes include ductal access probes, and wherein the step of establishing access comprises inserting one of said ductal access probes in each ductal orifice to be accessed.

3. A method as in claim 2, wherein at least some of the access probes are fluidly connected by a manifold so that substance may be delivered simultaneously to the connected probes through the manifold.

4. A method as in claim 3, wherein all of the access probes are fluidly connected to the manifold so that fluid may be delivered simultaneously to all probes.

5. A method as in claim 1, wherein the substance is delivered simultaneously to all of the accessed ductal networks.

6. A method as in claim 1, wherein fluid is collected in separate receptacles for each ductal network.

7. A method as in claim 1, wherein access is established to all of the ductal networks in a breast.

8. A method for lavaging two or more ductal networks in a breast, said method comprising:
   locating two or more ductal networks in a nipple of the breast;
   inserting an access probe through an orifice of each of the located ductal networks;
   infusing a lavaging fluid through a manifold to each of the probes and the respective accessed networks; and
   collecting a ductal fluid sample from within the accessed ductal networks using said access probes.

9. A method as in claim 8, further comprising connecting individual probes to the manifold so that the number of probes connected to the manifold is the same as the number of probes inserted into ductal orifices.

10. A method as in claim 8, further comprising providing an assembly comprising a number of access probes greater than the number of ductal orifices, wherein said access probes are pre-loaded on the manifold, and selectively blocking those access probes connected to the manifold which are not inserted into a ductal network.

11. A method as in claim 8, wherein said collecting step further comprises collecting fluid from each accessed ductal network, wherein the fluid is collected separately so that fluid from one of the ductal networks is free of fluid from another of the ductal networks.

12. A method for lavaging two or more ductal networks in a breast, said method comprising the steps of:
  locating at least two ductal networks in a nipple of the breast;
  providing an apparatus having a plurality of ductal network access probes;
  inserting one of the access probes through an orifice of each of the located ductal networks;
  closing any of the access probes that do not access one of the ductal networks;
  infusing the fluid through a manifold of said apparatus to each of the probes that accesses one of the ductal networks; and
  collecting ductal fluid from at least one of the accessed ductal networks using a respective one of said inserted access probes.

13. A method as in claim 12, further comprising the step of controlling a fluid flow through collection lumens, each said collection lumen being connected at a distal end to one of the probes that accesses one of the ductal networks and at a proximal end to a separate collection receptacle.

14. A method as in claim 13, wherein said collecting step further comprises collecting fluid in a respective one of the separate collection receptacles for each accessed duct.

15. A method as in claim 13, wherein the step of controlling a fluid flow through collection lumens comprises:
  closing fluid flow valves in the collection lumens corresponding to the access probes inserted in the ductal networks while fluid is infused into the accessed ductal networks;
  closing back flow valves in the access probes corresponding to the collection lumens; and
  opening the fluid flow valves for the collection lumens corresponding to the access probes inserted in the ductal networks to permit fluid flow from the ductal networks through the collection lumens and into the collection receptacles during the collecting ductal fluid step.

16. A method as in claim 15, further comprising massaging the breast just before and/or after the step of opening the fluid flow valves in the collection lumens.

* * * * *